(12) United States Patent
Gonzalez-Hernandez

(10) Patent No.: US 8,469,999 B2
(45) Date of Patent: Jun. 25, 2013

(54) SOFT TISSUE ATTACHMENT SYSTEM AND CLIP

(76) Inventor: Eduardo Gonzalez-Hernandez, Coconut Grove, FL (US)

( * ) Notice: Subject to any disclaimer, the term of this patent is extended or adjusted under 35 U.S.C. 154(b) by 0 days.

(21) Appl. No.: 13/439,717

(22) Filed: Apr. 4, 2012

(65) Prior Publication Data

US 2012/0197305 A1 Aug. 2, 2012

Related U.S. Application Data

(63) Continuation of application No. 12/121,269, filed on May 15, 2008, now abandoned.

(60) Provisional application No. 61/045,860, filed on Apr. 17, 2008.

(51) Int. Cl.
*A61B 17/04* (2006.01)

(52) U.S. Cl.
USPC .......................................................... 606/232

(58) Field of Classification Search
USPC .......................... 606/139–145, 228, 232, 280
See application file for complete search history.

(56) References Cited

U.S. PATENT DOCUMENTS

| | | | |
|---|---|---|---|
| 2,500,370 A | 3/1950 | McKibbin | |
| 3,489,143 A | 1/1970 | Halloran | |
| 3,552,389 A | 1/1971 | Allgower et al. | |
| 3,579,831 A | 5/1971 | Stevens et al. | |
| 3,716,050 A | 2/1973 | Johnston | |
| 3,791,380 A | 2/1974 | Dawidowski | |
| 3,900,025 A | 8/1975 | Barnes, Jr. | |
| 4,535,768 A | 8/1985 | Hourahane et al. | |
| 4,683,878 A | 8/1987 | Carter | |
| 4,733,654 A | 3/1988 | Marino | |
| 4,776,330 A | 10/1988 | Chapman et al. | |
| 4,790,302 A | 12/1988 | Colwill et al. | |
| 4,794,919 A | 1/1989 | Nilsson | |
| 4,838,264 A | 6/1989 | Bremer et al. | |
| 4,858,602 A | 8/1989 | Seidel et al. | |
| 4,870,957 A * | 10/1989 | Goble et al. | 623/13.12 |
| 5,003,969 A | 4/1991 | Azer et al. | |
| 5,041,114 A | 8/1991 | Chapman et al. | |

(Continued)

FOREIGN PATENT DOCUMENTS

| | | |
|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — Sameh Boles
(74) *Attorney, Agent, or Firm* — Martin & Ferraro, LLP

(57) ABSTRACT

A suture attachment clip and method for assisting in the attachment or re-attachment of soft tissue to bone. The clip generally comprises a head having a shape suitable for allowing the passage of a suture during attachment of soft tissue to bone. One or more clips can be secured to a bone plate through a variety of means, including a snap configuration, a screw configuration, and a bendable prong configuration. The clip can also be continuous with an adjacent clip, thus forming a multi-clip assembly that can either be secured to a bone plate or secured directly to a bone without a bone plate.

20 Claims, 10 Drawing Sheets

U.S. PATENT DOCUMENTS

| | | |
|---|---|---|
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,128,744 B2 | 10/2006 | Weaver et al. |
| D536,453 S | 2/2007 | Young et al. |
| 7,220,246 B2 | 5/2007 | Raulerson |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 * | 3/2009 | Kaiser et al. .......... 606/232 |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Wantanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady, Jr. et al. |
| 7,951,178 B2 | 5/2011 | Jensen |
| D643,121 S | 8/2011 | Milford et al. |
| D646,785 S | 10/2011 | Milford |
| 8,100,953 B2 | 1/2012 | White et al. |
| 8,182,485 B1 | 5/2012 | Gonzalez-Hernandez |
| 2003/0135216 A1 | 7/2003 | Sevrain |
| 2005/0004574 A1 | 1/2005 | Muckter |
| 2005/0021033 A1 * | 1/2005 | Zeiler et al. .......... 606/70 |
| 2005/0267476 A1 | 12/2005 | Chervitz et al. |
| 2006/0015072 A1 | 1/2006 | Raulerson |
| 2006/0015101 A1 | 1/2006 | Warburton et al. |
| 2006/0161156 A1 | 7/2006 | Orbay |
| 2006/0235400 A1 | 10/2006 | Scheider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2007/0016205 A1 | 1/2007 | Buetter et al. |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0264936 A1 | 10/2009 | Gonzalez-Hernandez et al. |
| 2009/0275991 A1 | 11/2009 | Medoff |
| 2009/0281578 A1 | 11/2009 | Spencer |
| 2010/0145339 A1 | 6/2010 | Steffen |
| 2010/0274245 A1 | 10/2010 | Gonzalez-Hernandez |
| 2011/0152943 A1 | 6/2011 | Gonzalez-Hernandez |
| 2012/0083848 A1 | 4/2012 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 468 655 A2 | 10/2004 |
| FR | 2 606 268 A1 | 5/1988 |
| FR | 2 680 673 A1 | 3/1993 |
| JP | 4-138152 A | 5/1992 |
| WO | WO 2005/037117 | 4/2005 |
| WO | WO 2008/007194 A2 | 1/2008 |

OTHER PUBLICATIONS

U.S. Appl. No. 11/050,304, filed Feb. 2005, Gonzalez-Hernandez.
U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.

U.S. Appl. No. 11/707,775, filed Feb. 2007, Gonzalez-Hernandez.
U.S. Appl. No. 13/253,564, filed Oct. 2011, Gonzalez-Hernandez.
U.S. Appl. No. 13/282,810, filed Oct. 2011, Gonzalez-Hernandez.
U.S. Appl. No. 13/411,069, filed Mar. 2012, Gonzalez-Hernandez.
U.S. Appl. No. 13/411,100, filed Mar. 2012, Gonzalez-Hernandez.
U.S. Appl. No. 13/412,039, filed Mar. 2012, Gonzalez-Hernandez.
Acumed; The Mayo Clinic Congruent Elbow Plates (catelog); 2003; 19 pages.
Acumed; The Mayo Clinic Congruent Elbow Plate System (catalog); Apr. 2006; 20 pages.
Christie, J., C.R. Howie and P.C. Armour, Fixation of displaced subcapital femoral fractures. Compression screw fixation versus double divergent pins. *J Bone Joint Surg [Br]* 1988; 70-B 199-201.
Cross W.M. et al., "Achieving stable fixation: biochemical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004, vol. 50, Issue 2; pp. 113-114, Accessed Aug. 6, 2008 at: http://www.jpgmonline.com/article.asp?issn=0022-3859;year=2004;volume=50;issue=2;spage=113;epage=114;aulast=Guha.
Hand Innovation, LLC; DVR Anatomic, Volar Plating System; 2007; 4 pages.
Robert, III, K.Q., R. Chandler, R,V, Barratta, K.A. Thomas and M.B. Harris The effect of divergent screw placement on the initial strength of plate-to-bone fixation, *J Trauma*, Dec. 2003;55(6):1139-44.

Synthesis; Locking Compression Plate (LCP) System (brochure); 2003; 6 pages.
Synthesis; Locking Compression Plate (LCP) System (brochure); Jan. 2007; 6 pages.
Written Opinion of the International Searching Authority; International Application No. PCT/US2009/036211; Sep. 23, 2010; 8 pages.
"Zimmer® Universal Locking System," The Journal of Bone and Joint Surgery, vol. 89, No. 7, Jul. 2007, 1 page.
Zimmer, Inc. "Zimmer Holdings to Launch Innovative Locking Plate System at Orthopaedic Trauma Association Meeting," Sep. 14, 2006; 3 pages.
Zimmer; Zimmer Periarticular Plating System-Low-Profile Fixation (catalog); 2003; 8 pages.
Postak, Paul D.; "Biomechanical Properties of Fixed-Angle Volar Distal Radius Plates Under Dynamic Loading;" 2007; 6 pages.
Synthes, "Large Fragment LCP instrument and Implant Set;" technique guide: 2003; 31 pages.
Synthes, "Locking Compression Plate (LCP) System. Locking screw technology and conventional plating in one system;" 2003; 6 pages.
Synthes; Modular Mini Fragment LCP System (brochure); 2007; 12 pages.
Synthes; Small Fragment Locking Compression Plate (LCP) System (brochure); 2002; 43 pages.
Zimmer, Inc. "Zimmer® Universal Locking System," brochure (2006), 4 pages.

* cited by examiner

SOFT TISSUE ATTACHMENT SYSTEM AND CLIP

The present application is a continuation of U.S. application Ser. No. 12/121,269, filed May 15, 2008 now abandoned; which claims the benefit of U.S. Provisional Application No. 61/045,860, filed on Apr. 17, 2008; all of which are incorporated by reference herein.

BACKGROUND OF THE INVENTION

1. Field of the Invention

The present invention relates to orthopedic devices used in the reattachment of soft tissue to bone in acute injuries or reconstructive procedures.

2. Description of the Prior Art

The present device and method provides a significant improvement for soft tissue attachment or reattachment to bone in acute injury or in reconstructive procedures. The various embodiments of the present invention can be used in conjunction with bone plates or by itself.

Musculoskeletal injuries constitute combinations of bone and soft tissue injury. As such, bone fractures frequently have associated tendon or ligament tears. Fractures around joints—know in the art as periarticular fractures—are classic examples of combined bone and tendon, or bone and ligament injuries. Existing plate systems utilized in orthopaedic surgical procedures, such as fracture fixation or reconstruction procedures, provide limited options for incorporating additional soft tissue anchoring into the plate. In most instances the plates designed for use in periarticular fracture procedures will have a few small orifices for the passage of a curved surgical needle. A torn or avulsed tendon can be reattached to the bone at the time of fracture fixation through the small orifices on the plates. Often, the small amount and small size of the orifices on the plate are not sufficient to repair significant soft tissue components. In addition, it is often very difficult to pass a needle, curved or straight, through these orifices once the plate has been screwed to the bone. Accordingly, existing bone plates provide limited options for soft tissue reattachment.

While the clinical success of bone anchors for the reattachment of tendon or ligament in musculoskeletal reconstruction is well documented, most existing bone anchors fail where the bone is very soft—as, or example, in severe osteopenia—or where the bone is very fragmented—as, for example, in fractures with severe bone fragmentation or comminution. In these instances, traditional bone anchors are inadequate for the reattachment of tendons and ligaments to bone.

It is therefore an object of the present invention to broaden the usefulness of bone plates by introducing additional features to plate design and fabrication that facilitate the reattachment of soft tissue, tendons, and ligaments to bone. The present invention has applications in fracture situations, and reconstructive procedures alike.

It is a further object of the present invention to provide a means of soft tissue reattachment or attachment to bone that can be used by itself without a bone plate; specifically, when other traditional methods, such as bone anchors, will not provide sufficient strength for repair.

SUMMARY OF THE INVENTION

The present invention generally comprises a suture attachment clip having various embodiments which provide multiple options for soft tissue repair to a bone structure.

In one embodiment of the present invention, the suture attachment clip comprises a head suitably shaped to allow the passage of a suture during the attachment of soft tissue to bone. A plurality of individual clips can attach to a bone plate by snapping the respective clips into corresponding receiving orifices on the bone plate, preferably located on the side of the bone plate. The clips can be attached to the bone plate at the time of manufacture or at the time of surgery.

In another embodiment of the present invention, the plurality of individual clips are attached to the bone plate by screwing each respective clip into a corresponding receiving orifice on the bone plate, preferably located on the side of the bone plate and preferably threaded internally. The clips can be screwed into the bone plate at the time of manufacture or at the time of surgery.

In yet another embodiment of the present invention, the plurality of individual clips are attached to a bone plate by inserting a free end of each respective clip through a corresponding pair of receiving orifices in the bone plate, preferably located on the side of the bone plate. The free ends of the clip are then bent through a corresponding pair of exit orifices on the bone plate, wherein the clip is fixed in place. In this embodiment, a clip can be designed and manufactured specifically to fit an existing bone plate's orifices, or alternatively, the bone plate and clip can be simultaneously and compatibly designed and manufactured. Each clip has a head suitably shaped to allow the passage of a suture during the repair of soft tissue to bone. The clips can be attached to the bone plate at the time of manufacture or at the time of the actual surgery.

In yet another embodiment of the present invention, the terminal end of one suture attachment clip is continuous with the terminal end of an adjacent suture attachment clip, thus forming a single multi-clip assembly. Each clip of the multi-clip assembly has a head suitably shaped to allow the passage of a suture during the attachment of soft tissue to bone. The multi-clip assembly attaches to the bone plate by snapping the multi-clip assembly to corresponding receiving channels on the bone plate. The receiving channels are preferably located on the undersurface of the bone plate. To further secure the multi-clip assembly to the bone plate, the multi-clip assembly could alternatively be fastened to the bone plate by locking screws or fasteners. Depending on the fastening method used, the multi-clip assembly can be attached to the bone plate at the time of manufacture or at the time of the actual surgery.

The multi-clip assembly can also be used without attachment to a bone plate. In this embodiment of the present invention, the multi-clip assembly is fastened to the bone with standard bone screws or fasteners through a plurality of eyelets positioned at various points on the multi-clip assembly.

These and other objects of the present invention will be apparent from review of the following specification and the accompanying drawings.

DETAILED DESCRIPTION OF THE PREFERRED EMBODIMENT

Figure 1:
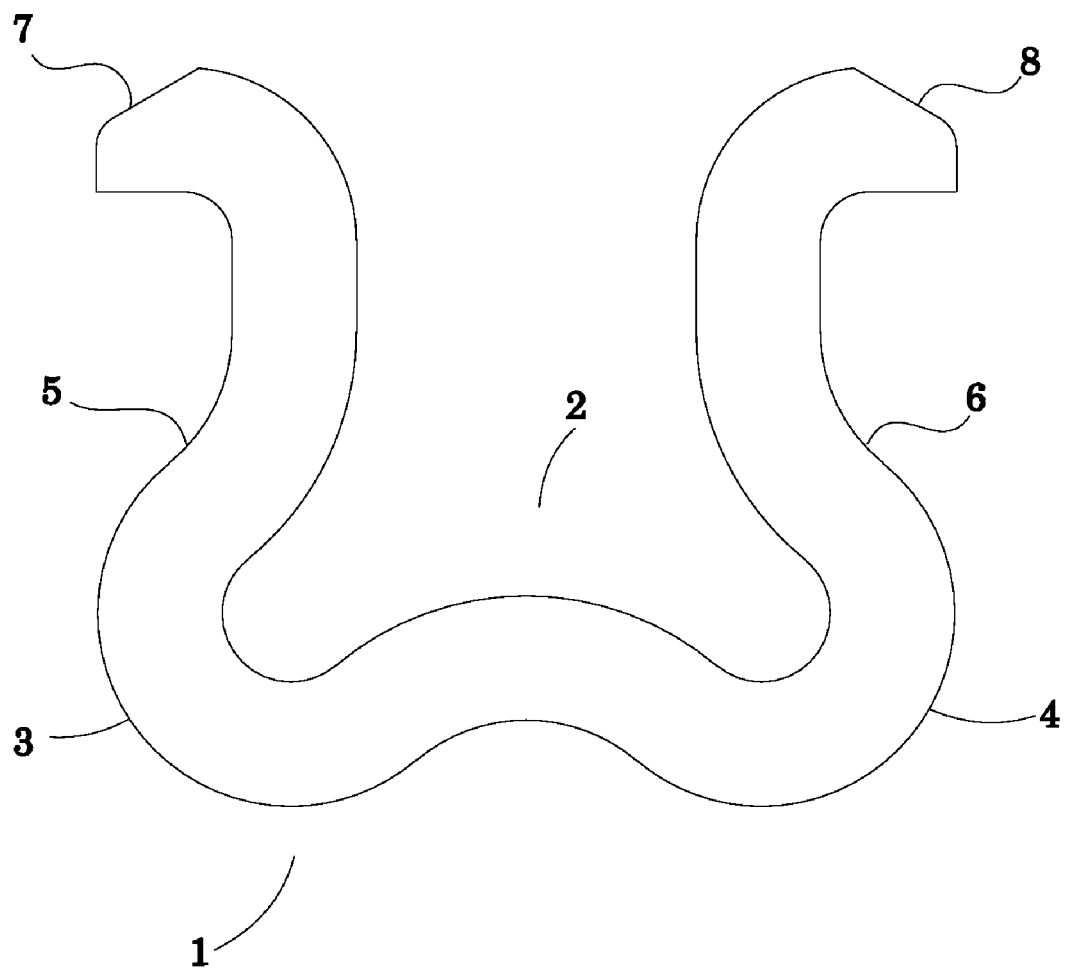
FIG. 1 illustrates a top perspective view of an individual clip with a snap configuration.

As shown in FIG. 1, in one embodiment of the present invention, the suture attachment clip 1 comprises a head 2 suitably shaped to allow the passage of a suture during the attachment of soft tissue to bone. In this embodiment, the head 2 preferably has a first and second lobe 3 and 4. In a preferred embodiment of the present invention, the first and second lobes 3 and 4 are symmetrical with respect to one another. In a preferred embodiment of the present invention, first and second lobes 3 and 4 are continuous with first and second prongs 5 and 6 wherein first prong 5 has a first outwardly protruding terminal end 7 and second prong 6 has a second outwardly protruding terminal end 8. Preferably, the head 2, prongs 5 and 6, and terminal ends 7 and 8 form an inverse-omega shape when clip 1 is viewed from the top perspective depicted in FIG. 1.

Figure 2:
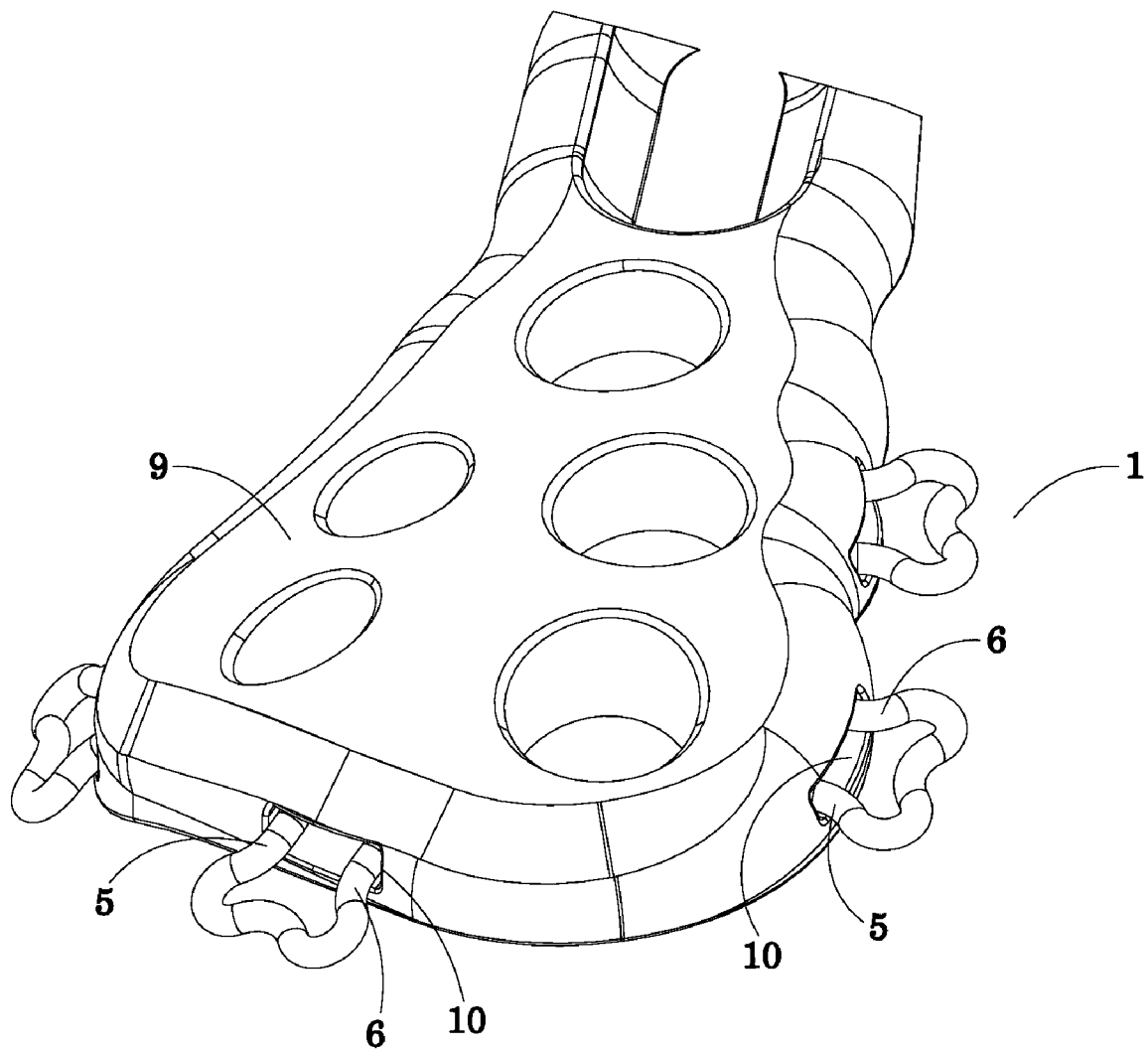
FIG. 2 illustrates a plurality of individual clips with snap configurations attached to a bone plate.

As shown in FIG. 2, a plurality of individual clips 1 can attach to a bone plate 9 by snapping prongs 5 and 6 of each respective clip 1 into a corresponding receiving orifice 10 on the bone plate 9. The receiving orifice 10 is preferably located on the edge of the bone plate 9. In this snapping configuration, pressure is applied to the prongs 5 and 6 so that the prongs are squeezed toward one another until each terminal end 7 and 8 can pass through the receiving orifice 10. When terminal ends 7 and 8 have sufficiently passed through the receiving orifice 10, pressure on the prongs 5 and 6 is released so that the prongs contact the edges of the receiving orifice 10, thereby securing the clip 1 to the bone plate 9. On or more clips 1 can be attached to the bone plate at the time of manufacture or at the time of surgery.

Figure 3:
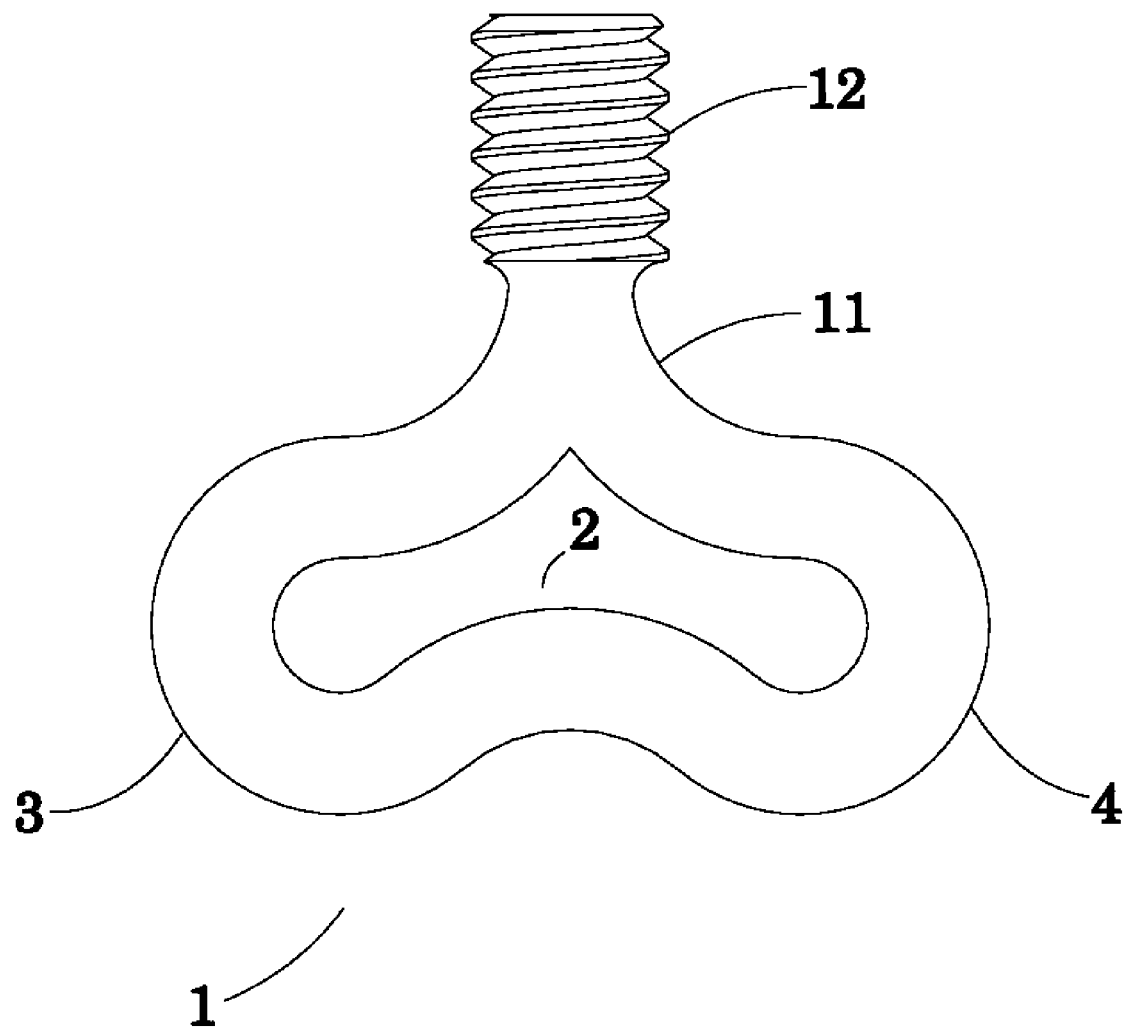
FIG. 3 illustrates a top perspective view of an individual clip with a threaded screw configuration.

As shown in FIG. 3, in another embodiment of the present invention, the suture attachment clip 1 comprises a head 2 suitably shaped to allow the passage of a suture during the attachment of soft tissue to bone. In this embodiment, the head 2 preferably has a first and second lobe 3 and 4 which fuse into a single prong 11. In a preferred embodiment of the present invention, the first and second lobes 3 and 4 are symmetrical with respect to one another. In a preferred embodiment of the present invention, single prong 11 has external threading 12.

Figure 4:
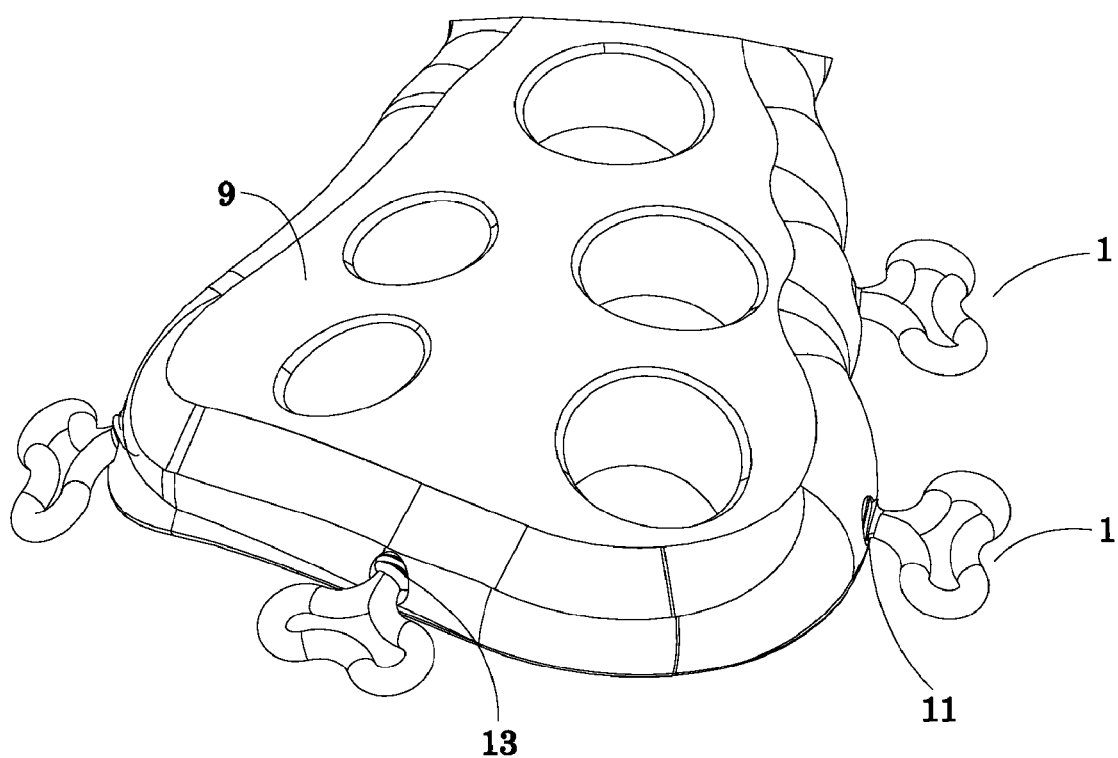
FIG. 4 illustrates a plurality of individual clips with threaded screw configurations attached to a bone plate.

As shown in FIG. 4, in the threaded screw configuration of the present invention, a plurality of individual clips 1 are attached to a bone plate 9 by screwing the single prong 11 of each respective clip 1 into a corresponding receiving orifice 13 on the bone plate 9, thereby securing the clip 1 to the bone plate 9. The receiving orifice 13 is preferably located on the edge of the bone plate 9 and is preferably threaded internally. On or more clips 1 can be screwed into the bone plate at the time of manufacture or at the time of surgery.

Figure 5:
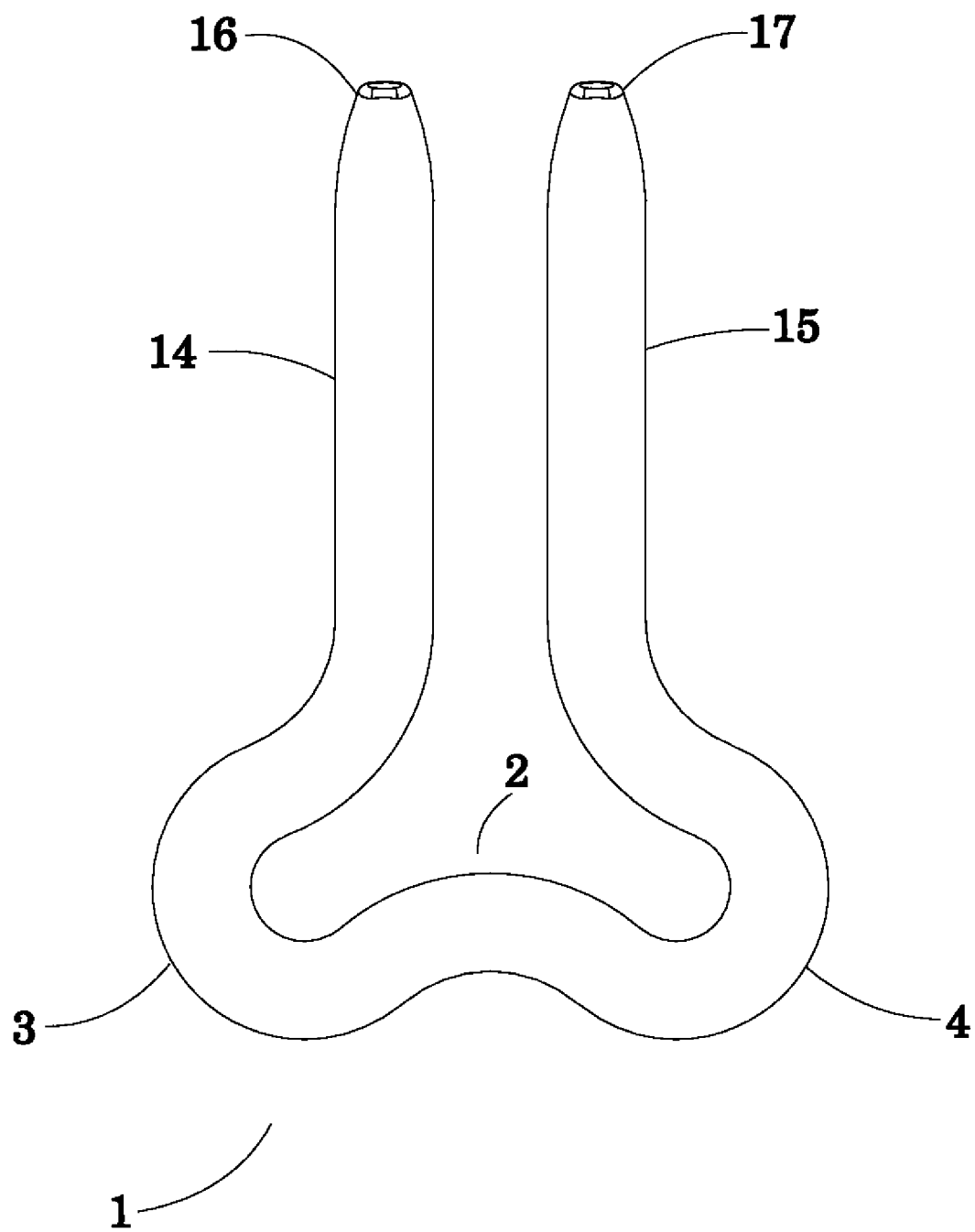
FIG. 5 illustrates a top perspective view of an individual clip with a dual prong configuration.

As shown in FIG. 5, in another embodiment of the present invention, the suture attachment clip 1 comprises a head 2 suitably shaped to allow the passage of a suture during the attachment of soft tissue to bone. In this embodiment, the head 2 preferably has a first and second lobe 3 and 4. In a preferred embodiment of the present invention, the first and second lobes 3 and 4 are symmetrical with respect to one another. In a preferred embodiment of the present invention, first and second lobes 3 and 4 are continuous with first and second bendable prongs 14 and 15. In a preferred embodiment of the present invention, the first bendable prong 14 is parallel to the second parallel prong 15. In a preferred embodiment of the present invention, first bendable prong 14 is continuous with first terminating end 16, and second bendable prongs 15 is continuous with second terminating end 17.

Figure 6:
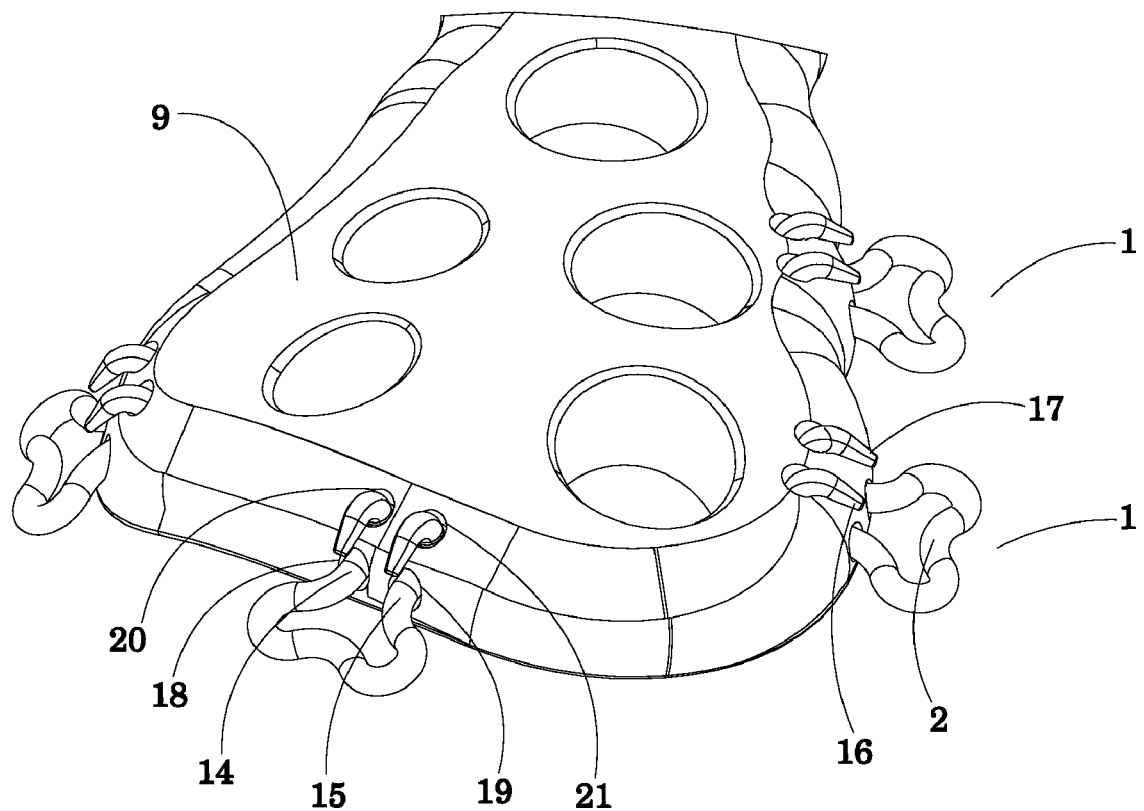
FIG. 6 illustrates a plurality of individual clips with bendable prong configurations attached to a bone plate.

As shown in FIG. 6, in the bendable prong configuration of the present invention, a plurality of individual clips 1 are attached to a bone plate 9 by inserting bendable prongs 14 and 15 of each respective clip 1 through corresponding first and second receiving orifices 18 and 19 in the bone plate. Receiving orifices 18 and 19 are preferably located on the edge of bone plate 9. In this embodiment, bendable prongs 14 and 15 are bent through corresponding first and second exit orifices 20 and 21 on the bone plate 9. Exit orifices 20 and 21 are preferably located on the edge of bone plate 9. As shown in FIG. 6, when bendable prongs 14 and 15 are bent through exit orifices 20 and 21, first and second terminating ends 16 and 17 face away from the bone plate 9 and toward the head 2 of the clip 1, thus securing the clip 1 to the bone plate 5. In this embodiment, clip 1 can be designed and manufactured specifically to fit an existing bone plate's orifices, or alternatively, the bone plate and one or more clips can be simultaneously and compatibly designed and manufactured. One or more clips 1 can be attached to the bone plate at the time of manufacture or at the time of the actual surgery.

Figure 7:
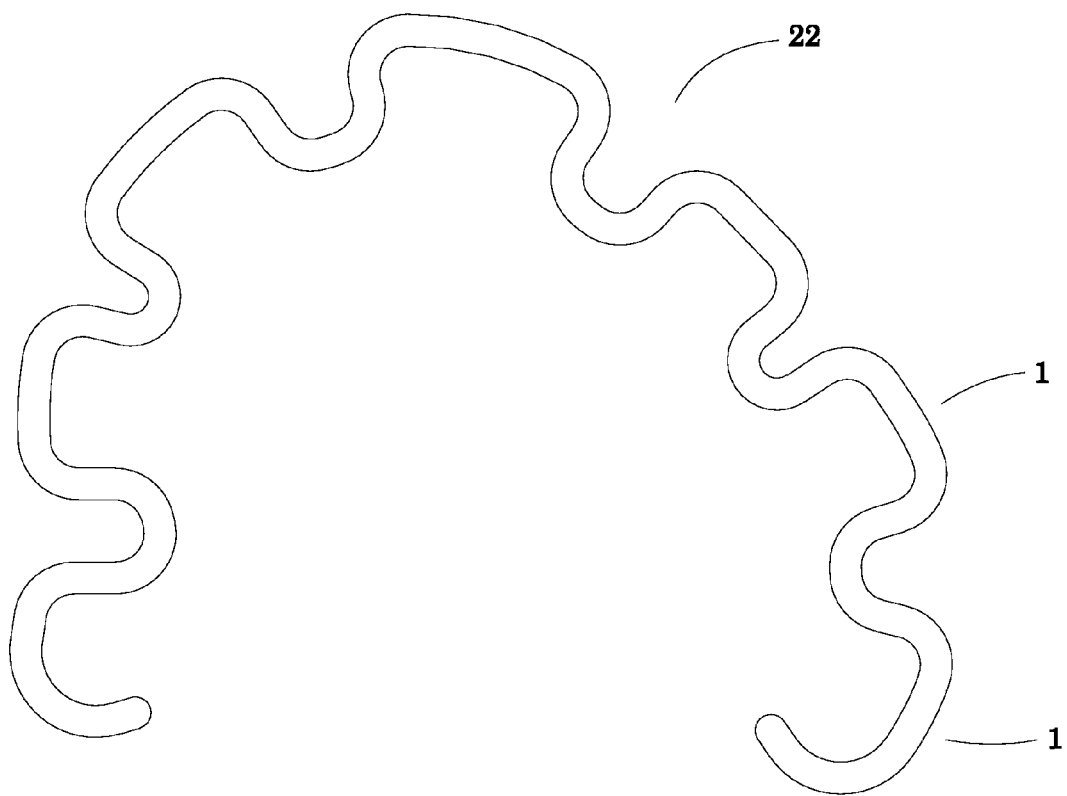
FIG. 7 illustrates a top perspective view of a multi-clip assembly.
Figure 8:
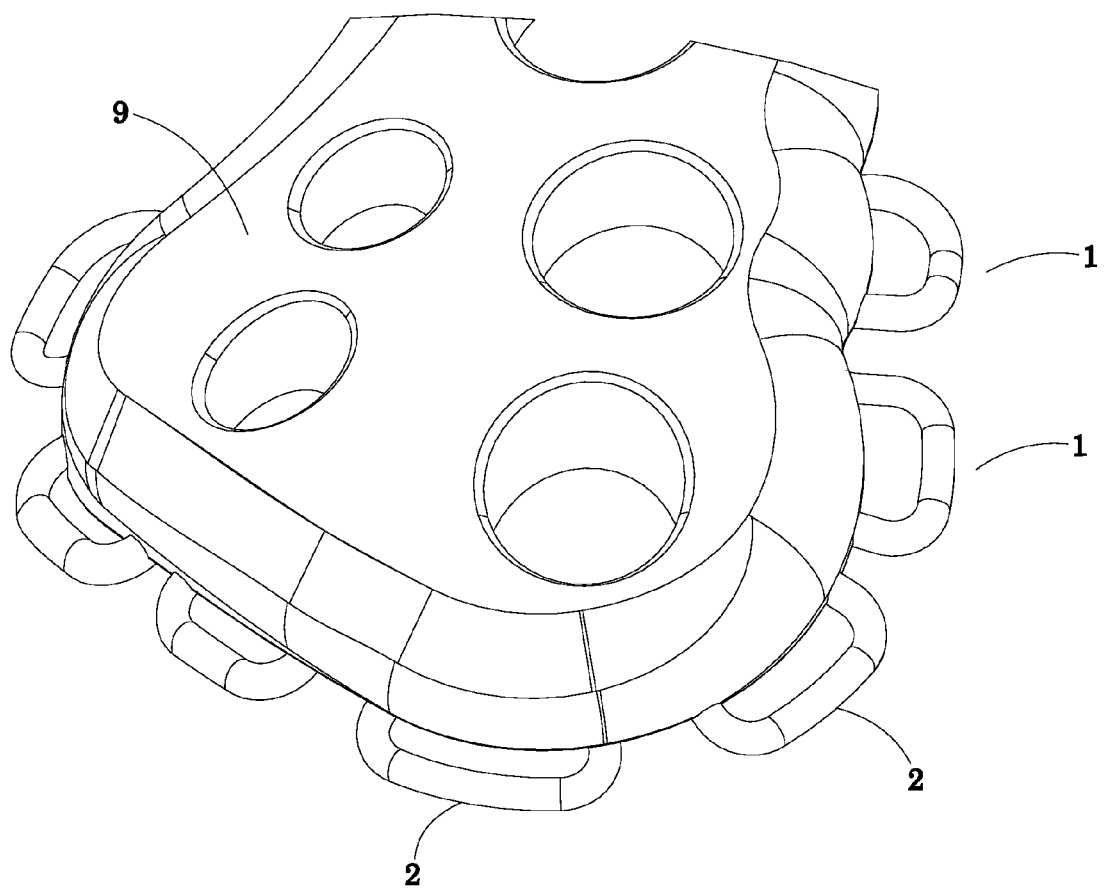
FIG. 8 illustrates a top perspective view of a bone plate with the multi-clip assembly attached to the underside of the bone plate.
Figure 9:
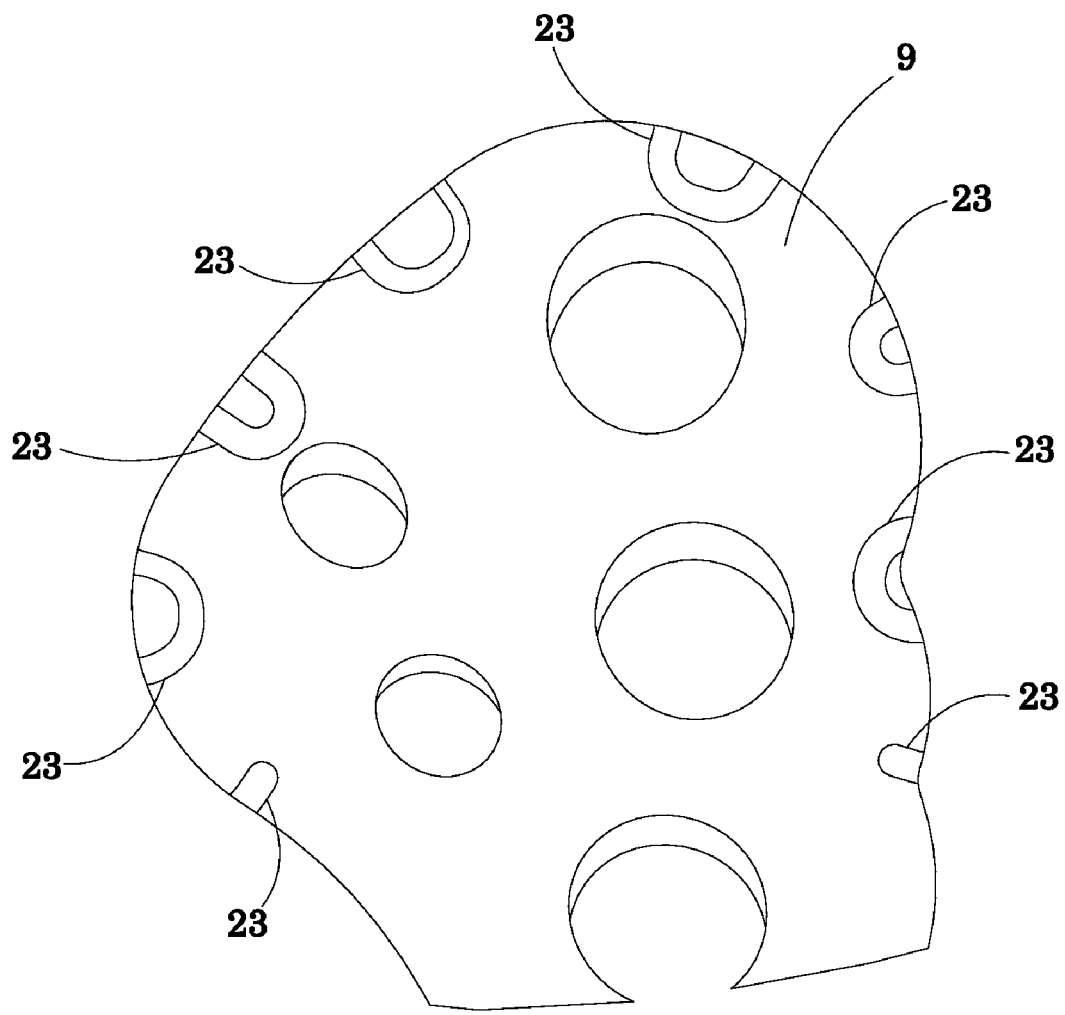
FIG. 9 illustrates a bottom view of a bone plate with a receiving channel for the multi-clip assembly.

As shown in FIG. 7, in yet another embodiment of the present invention, at least one terminal end of each clip 1, as depicted in FIG. 1, is continuous with the terminal end of an adjacent clip. The process can be repeated to form a plurality of linked clips, or a multi-clip assembly 22. Each clip 1 has a head suitably shaped to allow the passage of a suture during the attachment of soft tissue to bone. As shown in FIGS. 8 and 9, the multi-clip assembly 22 can preferably attach to the bone plate 9 by snapping the multi-clip assembly to corresponding receiving channels 23 on the bone plate 9. The receiving channels 23 are preferably located on the undersurface of the bone plate 9. While any portion of the multi-clip assembly can interlock with the corresponding receiving channels 23, as shown in FIG. 8, in a preferred embodiment of the present invention, a portion of the head 2 of each clip 1 linked together in the multi-clip assembly 22 should remain sufficiently exposed beyond the edge of the bone plate 9 in order to allow for the passage of a suture.

To further secure the multi-clip assembly 22 to the bone plate 9, the multi-clip assembly could alternatively be fastened to the bone plate by locking screws or fasteners. Depending on the fastening method used, the multi-clip assembly can be attached to the bone plate at the time of manufacture or at the time of the actual surgery.

Figure 10:
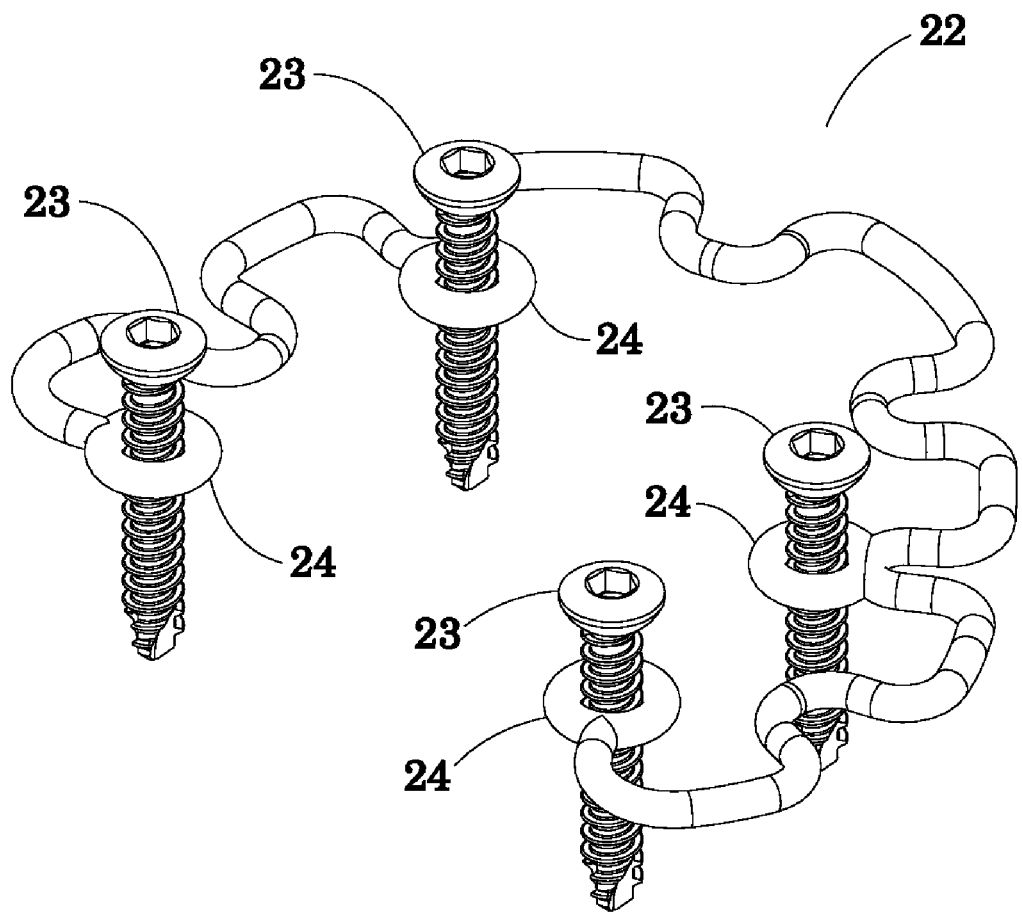
FIG. 10 illustrates a perspective view of the multi-clip assembly with eyelets and bone screws for attachment without a bone plate.

As shown in FIG. 10, the multi-clip assembly 22 can also be used without a bone plate. In this embodiment of the present invention, the multi-clip assembly 22 is fastened to the bone by inserting standard bone screws 23 or fasteners through a plurality of eyelets 24 positioned at various points on the multi-clip assembly 22, preferably at the juncture of the respective terminal ends of each linked individual clip 1 within the multi-clip assembly 22.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A system for attaching soft tissue to bone, said system comprising:
   a bone plate having a perimeter, a lower surface for placement against the bone, an upper surface opposite said lower surface, at least two holes extending through said bone plate from said upper surface to said lower surface, a first orifice and a second orifice formed in said bone plate on a perimeter of said bone plate, and a third orifice and a fourth orifice formed in said bone plate, each of said first, second, third, and forth orifices being adapted to receive a portion of a suture attachment clip;
   at least one suture attachment clip including a first shaft, a second shaft, a head portion, and a mid-longitudinal axis extending between said first and second shafts and through said head portion, said head portion including a first lobe portion and a second lobe portion, said first shaft adapted to be inserted into said first orifice and protrude outwardly from said third orifice, and said second shaft adapted to be inserted into said second orifice and protrude outwardly from said fourth orifice, said first shaft being wrapped around a first portion of said bone plate between said first and third orifices to attach said first shaft to said bone plate, and said second shaft being wrapped around a second portion of said bone plate between said second and fourth orifices to attach said second shaft to said bone plate;
   an opening formed in said head portion for receiving a suture therethrough, said opening including a first concave arcuate side corresponding to said first lobe portion and a second concave arcuate side corresponding to said second lobe portion; and
   a perimeter of said head portion in a first plane extending through the mid-longitudinal axis, said first lobe portion, said second lobe portion, and said first connecting portion, said perimeter having a first convex arcuate side corresponding to said first lobe portion and a second convex arcuate side corresponding to said second lobe portion.

2. The system of claim 1, wherein said at least one suture attachment clip further comprises a first connecting portion extending between said first and second lobe portions, a convex side of said opening, and a concave side of said perimeter, said convex side of said opening and said concave side of said perimeter corresponding to said first connecting portion.

3. The system of claim 2, further comprising a second connecting portion and a third connecting portion, said second connecting portion being connected to said first lobe portion and terminating in said first shaft, said third connecting portion being connected to said second lobe portion and terminating in said second shaft.

4. The system of claim 1, wherein said first lobe portion and said second lobe portion are symmetrical to one another about a second plane perpendicular to said first plane, said second plane extending through the mid-longitudinal axis.

5. The system of claim 4, wherein said at least one suture attachment clip includes a maximum length parallel to the mid-longitudinal axis, and a maximum width perpendicular to said maximum length, said maximum width of said at least one suture attachment clip being the maximum dimension of said head portion.

6. The system of claim 5, wherein the maximum distance between said first and second shafts in a third plane perpendicular to said first and second planes is less than the maximum dimension of said head portion.

7. A system for attaching soft tissue to bone, said system comprising:
   a bone plate having a perimeter, a lower surface for placement against the bone, an upper surface opposite said lower surface, at least two holes extending through said bone plate from said upper surface to said lower surface, a first orifice and a second orifice formed in said bone plate on a perimeter of said bone plate, and a third orifice and a fourth orifice formed in said bone plate, each of said first, second, third, and fourth orifices being adapted to receive at least a portion of a suture attachment clip;
   at least one suture attachment clip including a first shaft, a second shaft, a head portion, and a mid-longitudinal axis extending between said first and second shafts, said head portion including a first arcuate portion extending around a first axis, a second arcuate portion extending around a second axis, and a first connecting portion extending between said first and second arcuate portions, said first and second axes being offset from one another on opposite sides of the mid-longitudinal axis, said first shaft adapted to be inserted into said first orifice and protrude outwardly from said third orifice, and said second shaft adapted to be inserted into said second orifice and protrude outwardly from said fourth orifice, said first shaft being wrapped around a first portion of said bone plate between said first and third orifices to attach said first shaft to said bone plate, and said second shaft being wrapped around a second portion of said bone plate between said second and fourth orifices to attach said second shaft to said bone plate;
   an opening formed in said head portion for receiving a suture therethrough, said opening extending through a first plane, said first plane extending through said first arcuate portion, said second arcuate portion, and the mid-longitudinal axis, said opening including a first concave side in said first plane corresponding to said first arcuate portion, and a second concave side in said first plane corresponding to said second arcuate portion; and
   a perimeter of said head portion, said perimeter being in said first plane, said perimeter having a first convex side in said first plane corresponding to said first arcuate portion, and a second convex side in said first plane corresponding to said second arcuate portion.

8. The system of claim 7, wherein said at least one suture attachment clip further comprises a convex side of said opening in said first plane, and a concave side of said perimeter in said first plane, said convex side of said opening and said concave side of said perimeter corresponding to said first connecting portion.

9. The system of claim 7, wherein said at least one suture attachment clip includes a leading end, and an opposite trailing end, said first and second shafts extending from proximate said first and second arcuate portions toward said leading end.

10. The system of claim 9, wherein said at least one suture attachment clip includes a maximum length parallel the mid-longitudinal axis, and a maximum width perpendicular to said maximum length, said maximum width of said at least one suture attachment clip being the maximum dimension of said head portion.

11. The system of claim 7, wherein said at least one suture attachment clip includes a maximum length parallel the mid-longitudinal axis, and a maximum width perpendicular to the maximum length, the maximum width of said at least one suture attachment clip being the maximum dimension of said head portion.

12. The system of claim 11, wherein said first arcuate portion and said second arcuate portion are symmetrical to one another about a second plane perpendicular to said first plane, said second plane extending through the mid-longitudinal axis.

13. The system of claim 12, wherein the maximum distance between said first and second shafts in a third plane perpendicular to said first and second planes is less than the maximum dimension of said head portion.

14. A system for attaching soft tissue to bone, said system comprising:
   a bone plate having a perimeter, a lower surface for placement against the bone, an upper surface opposite said lower surface, at least two holes extending through said bone plate from said upper surface to said lower surface, a first orifice and a second orifice formed in said bone plate on a perimeter of said bone plate, and a third orifice and a fourth orifice formed in said bone plate, each of said first, second, third, and fourth orifices being adapted to receive at least a portion of a suture attachment clip;
   at least one suture attachment clip including a first shaft, a second shaft, a head portion, and a mid-longitudinal axis extending between said first and second shafts, said head portion including a first C-shaped portion, a second C-shaped portion, and a first connecting portion extending between said first and second C-shaped portions, said first shaft adapted to be inserted into said first orifice and protrude outwardly from said third orifice, and said second shaft adapted to be inserted into said second orifice and protrude outwardly from said fourth orifice, said first shaft being wrapped around a first portion of said bone plate between said first and third orifices to attach said first shaft to said bone plate, and said second shaft being wrapped around a second portion of said bone plate between said second and fourth orifices to attach said second shaft to said bone plate;
   an opening formed in said head portion for receiving a suture therethrough, said opening extending through a first plane, said first plane extending through said first C-shaped portion, said second C-shaped portion, and the mid-longitudinal axis, said opening including a first portion defined in part by said first C-shaped portion and a second portion defined in part by said second C-shaped portion, sides of said first and second portions in said first plane each being arcuate; and
   a perimeter of said head portion, said perimeter being in said first plane, said perimeter having a first arcuate side in said first plane corresponding to said first arcuate portion, and a second arcuate side in said second plane corresponding to said second arcuate portion.

15. The system of claim 14, wherein said at least one suture attachment clip further comprises a convex side of said opening in said first plane, and a concave side of said perimeter in said first plane, said convex side of said opening and said concave side of said perimeter corresponding to said first connecting portion.

16. The system of claim 14, wherein said at least one suture attachment clip includes
   a leading end, and an opposite trailing end, said first and second shafts extending from proximate said first and second C-shaped portions toward said leading end.

17. The system of claim 16, wherein said at least one suture attachment clip includes a maximum length parallel the mid-longitudinal axis, and a maximum width perpendicular to said maximum length, said maximum width of said at least one suture attachment clip being the maximum dimension of said head portion.

18. The system of claim 14, wherein said at least one, suture attachment clip includes a maximum length parallel the mid-longitudinal axis, and a maximum width perpendicular to the maximum length, the maximum width of said at least one suture attachment clip being the maximum dimension of said head portion.

19. The system of claim 18, wherein said first C-shaped portion and said second C-shaped portion are symmetrical to one another about a second plane perpendicular to said first plane, said second plane extending through the mid-longitudinal axis.

20. The system of claim 19, wherein the maximum distance between said first and second shafts in a third plane perpendicular to said first and second planes is less than the maximum dimension of said head portion.

\* \* \* \* \*

UNITED STATES PATENT AND TRADEMARK OFFICE
CERTIFICATE OF CORRECTION

PATENT NO.         : 8,469,999 B2                          Page 1 of 1
APPLICATION NO.    : 13/439717
DATED              : June 25, 2013
INVENTOR(S)        : Eduardo Gonzalez-Hernandez It is certified that error appears in the above-identified patent and that said Letters Patent is hereby corrected as shown below:

Title Page 3, Item (56) References Cited, Other Publications, Column 1:
Line 7: change "(catelog)" to -- (catalog) --;
Line 13: change "70-B 199-201" to -- 70-B: 199-201 --;
Line 14: change "Cross" to -- Cross, --; and change "biochemical" to -- biomechanical --;
Line 22: change "Innovation" to -- Innovations --;
Line 25: change "Harris" to -- Harris, --;

Title Page 3, Item (56) References Cited, Other Publications, Column 2:
Lines 1 and 3: change "Synthesis" to -- Synthes --; and
Line 16: change "instrument" to -- Instrument --.

In the Claims:

Column 5, Claim 1:
Line 14: change "forth" to -- fourth --.

Column 8:
Claim 16: lines 16 and 17: rewrite without a paragraph break as follows: -- attachment clip includes a leading end, and an opposite trailing end, said first and --; and
Claim 18: line 26: change "one," to -- one --.

Signed and Sealed this
Eighteenth Day of February, 2014

Michelle K. Lee
*Deputy Director of the United States Patent and Trademark Office*